United States Patent

Ershov et al.

[11] Patent Number: 5,962,329
[45] Date of Patent: Oct. 5, 1999

[54] METHOD OF DISPENSING MICRODOSES OF AQUEOUS SOLUTIONS OF SUBSTANCES ONTO A CARRIER AND A DEVICE FOR CARRYING OUT SAID METHOD

[75] Inventors: Gennady Moiseevich Ershov, Moscow; Eugenii Vladislavovich Kirillov, gor. Dolgoprudnyi; Andrei Darievich Mirzabekov, Moscow, all of Russian Federation

[73] Assignee: University of Chicago, Chicago, Ill.

[21] Appl. No.: 09/061,308

[22] Filed: Apr. 16, 1998

Related U.S. Application Data

[63] Continuation of application No. 08/411,792, filed as application No. PCT/RU94/00179, Aug. 5, 1994, Pat. No. 5,756,050.

[30] Foreign Application Priority Data

Aug. 11, 1993 [RU] Russian Federation ............. 93040902

[51] Int. Cl.$^6$ ................................ G01N 1/12; G01N 1/02
[52] U.S. Cl. .............................. 436/50; 422/67; 422/100; 435/286.3; 435/286.4; 435/287.2; 435/309.1; 436/54; 436/55; 436/174; 436/179; 436/180; 436/94
[58] Field of Search ................................. 422/67, 92, 95, 422/100, 102, 104, 65, 66; 436/174, 179, 180, 50, 54, 55, 94; 435/287.2, 309.1, 286.3, 286.4

[56] References Cited

U.S. PATENT DOCUMENTS

| | | | |
|---|---|---|---|
| 4,235,971 | 11/1980 | Howard et al. | 435/286.4 |
| 4,252,897 | 2/1981 | Axford et al. | 435/286.3 X |
| 4,272,381 | 6/1981 | Kremer et al. | 210/658 |
| 4,480,031 | 10/1984 | Shaw | 435/286.4 X |
| 4,635,488 | 1/1987 | Kremer | 73/864.72 |
| 4,659,677 | 4/1987 | Glover et al. | 436/174 |
| 5,223,225 | 6/1993 | Gautsch | 422/100 |
| 5,436,129 | 7/1995 | Stapleton | 435/6 |
| 5,443,791 | 8/1995 | Cathcart et al. | 422/65 |
| 5,756,050 | 5/1998 | Ershow et al. | 422/100 |

OTHER PUBLICATIONS

D.R. Bentley et al. *Genomics* 1992, 12, 534–541.
S. Drmanac et al. *Biotechniques* 1994, 17, 328–336.

*Primary Examiner*—Arlen Soderquist
*Attorney, Agent, or Firm*—Foley & Lardner

[57] ABSTRACT

A method and a device for dispensing microdoses of aqueous solutions are provided, whereby the substance is transferred by the free surface end of a rodlike transferring element; the temperature of the transferring element is maintained at essentially the dew point of the ambient air during the transfer. The device may comprise a plate-like base to which are affixed a plurality of rods; the unfixed butt ends of the rods are coplanar. The device further comprises a means for maintaining the temperature of the unfixed butt ends of the rods essentially equal to the dew point of the ambient air during transfer of the aqueous substance.

10 Claims, 4 Drawing Sheets

METHOD OF DISPENSING MICRODOSES OF AQUEOUS SOLUTIONS OF SUBSTANCES ONTO A CARRIER AND A DEVICE FOR CARRYING OUT SAID METHOD

This application is a continuation of application Ser. No. 08/411,792, filed May 26, 1995, now U.S. Pat. No. 5,756, 050, which was a 371 of PCT/RU94/00179, filed Aug. 5, 1994.

FIELD OF THE INVENTION

The present invention relates in general to biology and, more specifically, provides a method and a device for microdispensing of aqueous solutions of various substances to a carrier.

BACKGROUND OF THE INVENTION

One well-known method for microdispensing of aqueous solutions of substances onto a carrier uses rarefaction of the medium over the surface of the solution for filling a closed calibrated space, and excess pressure for ejecting said solution from the calibrated space back into solution or onto the surface of a carrier. A device for carrying said method into effect comprises a precision pair "cylinder-piston," wherein displacement of the piston with respect to the cylinder establishes rarefaction above the piston, thereby providing for filling the below-piston space with a microvolume of solution which is ejected from said space during the return piston stroke. An increased quantity of simultaneously prepared microvolumes is provided, using this method, by an increased number of parallel channels. The method under consideration and the device carrying it into effect are capable of microdispensing of the aqueous solution of substances in the range from tens of milliliters down to one microliter with an accuracy of 0.5% to 1% (cf. Cole-Parmer® micro and macropipettors; L-07839-51÷L-07839-76). Multichannel devices (Chempette® multichannel pipettes; L-07915-60) provide for microdispensing of quantities from tens of milliliters down to 5 $\mu l$, respectively, with an accuracy of 1.5 to 2%, the maximal number of parallel channels being 12.

The method discussed before and the device for its realization cannot be used for dispensing microvolumes lesser than one microliter. Moreover, said method and device have a rather low dispensing capacity (no more than 12 parallel channels).

Another method for microdispensing of aqueous solutions of substances onto a carrier is used in BIOMEK® 1000 Automated Laboratory Workstation (BECKMAN) and intended for high-quality transfer of clones, cell lines, bacteria, aqueous DNA solutions, etc. The method of microdispensing comprises use of a rodlike transferring element. The method consists in wetting the free end surface of the transferring element with an aqueous solution of substance to form a dose of said aqueous solution on said surface, followed by transferring said dose and bringing it in contact with the surface of the carrier. The method in question is based on the action of intermolecular interaction forces at the liquid-solid interface.

Also known is a device for carrying said method into effect.

The device comprises a plate-like base, one side of which carries 96 needle-like rods which are clamped thereto at one end, the other (butt) faces of said rods being coplanar (S91-8545-AP-20; 1991 Beckman Instrument Inc.; Bulletin No. 7883).

The layout of the rods on the plate corresponds exactly to the arrangement of the wells containing the solutions, on the tray. Two standard sizes of the rods are available, differing in the diameter of the end face (0.0015" tip pins—P/N 372172; 0.060" tip pins—PIN 372173; S91-8545-AP-20; 1991 Beckman Instument Inc., Bulletin No. 7883).

Microdoses of aqueous solutions of substances are transferred from the tray wells to the carrier as follows.

The plate carrying the rods are secured in a holder joined to the moving positioner head. By moving the head one positions the plate above the tray so that one rod is located over each well, whereupon the plate is moved down along the Z-axis. As a result, the rods dip into the tray wells to get wetted with the solutions contained therein. Thereupon the plate is moved up along the Z-axis, displaced spatially, and positioned above the carrier surface. Next the plate is moved down again along the Z-axis until the rod ends get in contact with the carrier surface, whereby the microdoses of the solutions of substances are transferred from the rod ends onto the carrier. Thereupon the rods are cleaned, sterilized, and dried, after which the cycle is repeated. Thus, 1536 samples are transferred to the carrier for about 30 minutes, that is, the known method and device make it possible to increase the dispensing capacity and that of transferring aqueous solutions of substances compared with the method and device discussed before. The capabilities of said method are, however, limited to the rate of evaporation of a microdose of liquid from the transferring element, that is, the rod.

When a single microvolume is as low as tens of nanoliters or less, the solution is liable to badly evaporate and its viscosity increases to such as extent that the dose of a solution cannot be transferred to the carrier, or such a microdose evaporates completely in the course of transferring. Moreover, inasmuch as the end and side surfaces of the rods in the known device feature the same magnitude of the wetting angle, the microvolumes of solutions are formed at the vacant ends of rods as microdrops which spread over the side rod surface as well, which place limitation upon the minimal volume of the solution being transferred. For the same reasons reproducibility of the microdrop volume is affected, since it depends on the rod dipping depth (that is, the dipping depth of the rod changes in response to a drop of the solution level in the wells).

SUMMARY OF THE INVENTION

The principal object of the invention is to modify conditions for carrying out the method for microdispensing of aqueous solutions of substances to a carrier so as to prevent evaporation of liquid from the rodlike transferring element, thereby making possible microdispensing of minimal doses of aqueous solutions with a higher accuracy and reproducibility, as well as to provide a device for carrying said method into effect, which is constructionally simple, reliable, and convenient in operation.

The foregoing object is accomplished due to the fact that in the herein-proposed method for microdispensing of aqueous solutions of substances to a carrier using a rodlike transferring element and comprising wetting of the end face of the transferring element with an aqueous solution of substance, forming on said surface a preset dose of said substance, followed by displacing said element until it contacts the carrier surface, according to the invention, the temperature of the aqueous solution of the substance and the temperature of the surface of the transferring element is maintained substantially equal to the dew point of the ambient air in the course of dose formation and its transference.

The herein-proposed method is applicable for microdispensing of any aqueous solutions of substances. Preferably use is made of an aqueous oligonucleotide solution. The herein-proposed method enables one to perform microdispensing of minimal (of the order of 0.3 nl) volumes of aqueous solutions of substances. It is due to a combination of the aforementioned conditions (i.e., maintaining the temperature of an aqueous solution of a substance and of the surface of the transferring element substantially equal to the dew point of the ambient atmosphere in the course of dose transference) that evaporation of the liquid is precluded, which contributes to higher accuracy and reproducibility of the microdispensing process, simplifies the techniques and rules out the dependence of the microvolume being transferred on the depth of immersion of the rods into the solution involved.

The foregoing object is accomplished also due to the fact that a device for microdispensing of aqueous solutions of substances to a carrier, comprising a plate-like base one of the sides thereof carries a plurality of rods which are held to said plate with one of their ends, the free butt ends of said rods be coplanar, according to the invention, is provided with a means for maintaining the temperature of the free butt ends substantially equal to the dew point of the ambient air.

It is preferable that used as said means for maintaining the temperature of said free butt ends be the battery of Peltier cells shaped as a plate having equal size with the plate of the base and contacting the latter on the side opposite to that carrying the rods. The platelike base and the rods are preferentially made of a highly thermal-conductive material. This makes the process for maintaining a preset temperature with a high degree of accuracy readily automated. In addition, the battery of Peltier cells is capable of switching the mode from cooling (rods maintenance of the dew point) to their heating (drying the rods after their cleaning and sterilization) by merely reversing the polarity of the direct current, which cuts down the cycle time and thereby contributes to higher capacity of the method, as well as to better accuracy and reproducibility thereof.

It is expedient that the base and rods be made of a metal having high thermal conductivity, which is conducive to rapid equalization of the rod temperature and, eventually, to reduction of the cycle time. To diminish heat ingress from the ambient atmosphere, it is desirable that the rod ends held to the plate and not contacting solutions, and the surface of the plate itself be provided with a heat-insulant coating.

It is reasonable that a hydrophilic coating be applied to the free butt ends of the rods, and that the side surfaces thereof be provided with a hydrophobic coating. This ensures that microvolumes of solutions will be formed only on the butt ends of the rods during their withdrawal from the solutions, thereby adding to the accuracy and reproducibility of the method.

It is preferable that the area of the butt end of each rod (for the round cross-section rods) be selected so as to obey to the following relationship: $V \approx \frac{1}{3}\pi R^3 \cdot 10^{-6}$ nl, where V is the required volume of the droplet being formed on the butt rod end after the rod has been withdrawn from the solution, $R(\mu m)$ being the radius of the butt rod end.

To ensure the desired accuracy and reproducibility of the method, it is expedient that the butt rod ends be glass-coated, and the side rod surfaces be coated with fluoroplastic.

According to an alternative embodiment of the device, with the purpose of providing the required accuracy and reproducibility of the process, it is expedient that the vacant rod ends be glass-coated and the side rod surface be treated with Repel Silane.

The device proposed herein has a simple design, convenience in operation and required no expensive materials and components for its manufacture.

A BRIEF DESCRIPTION OF THE DRAWINGS

In what follows the invention is illustrated by a detailed description of some specific embodiments thereof with reference to the accompanying drawings, wherein.

DESCRIPTION OF PREFERRED EMBODIMENTS OF THE INVENTION

The method disclosed herein can find application in microdispensing of aqueous solutions, containing biological components, DNA fragments, chromosomes, cells and others, as well as for microdispensing of pigments, dyes, and so on. However, the method proposed herein is most suitable to be applied for microdispensing of aqueous solutions of oligonucleotides to a carrier. The present method for microdispensing of aqueous solutions of substances, according to the invention, is carried into effect as follows. The butt end of the rodlike transferring element is wetted with an aqueous solution of a substance, said solution being located in the tray well. Then the dose of the solution thus formed on the surface of the butt rod end is transferred and brought in contact with the carrier surface (that is, matrix with gel areas) to which the dose is transferred. The temperature of the aqueous solution of the substance and the temperature of the surface of the transferring element are maintained during the process substantially equal to the dew point of the ambient air, i.e. equal to the temperature to which the atmospheric air is to be cooled down in order that the vapor contained therein becomes saturated and starts condensing.

This enables one to avoid evaporation of the liquid when a preset dose of the substance is formed on the butt end surface of the transferring element and is then transferred, thereby adding to the accuracy and reproducibility of the proposed method of microdispensing of the minimal volumes of solutions of substances.

Figure 1:
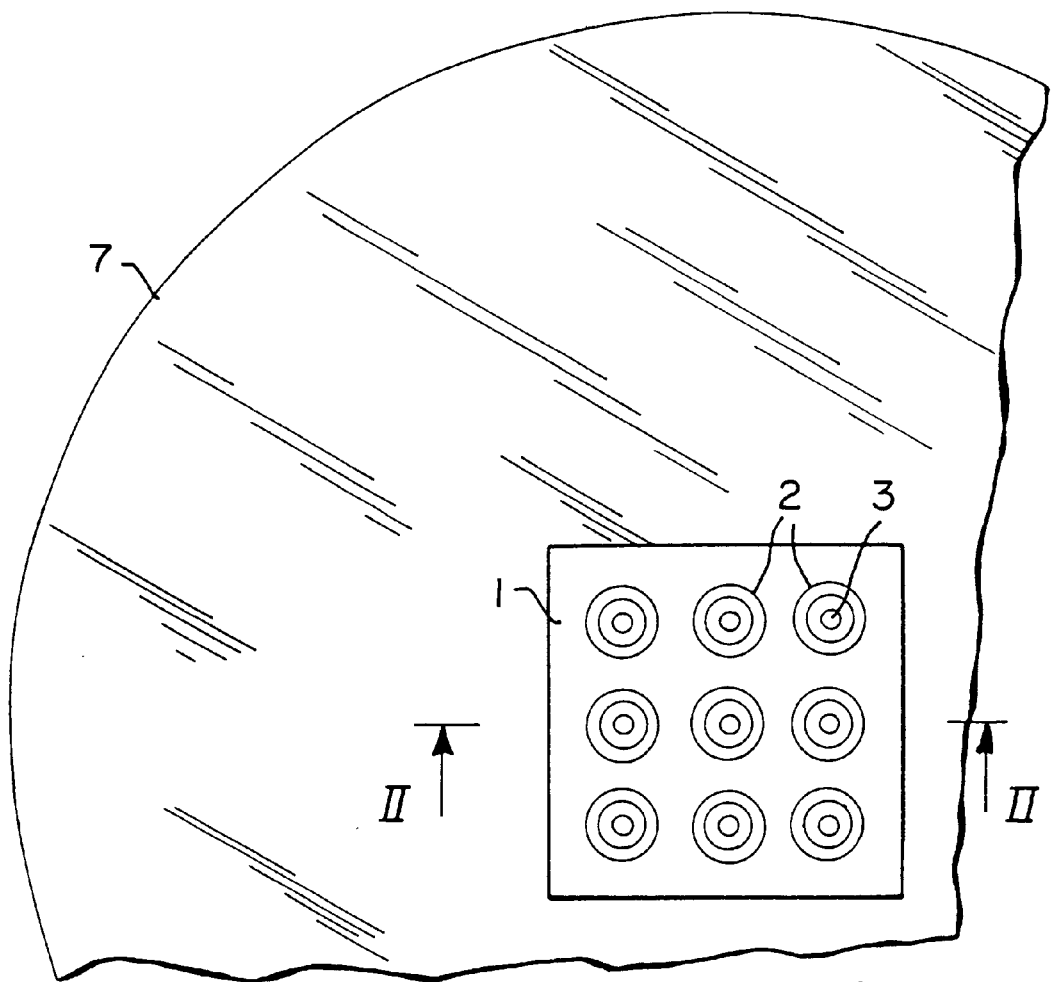
FIG. 1 is a plan view of the device for microdispensing of aqueous solutions of substances to a carrier.
Figure 2:
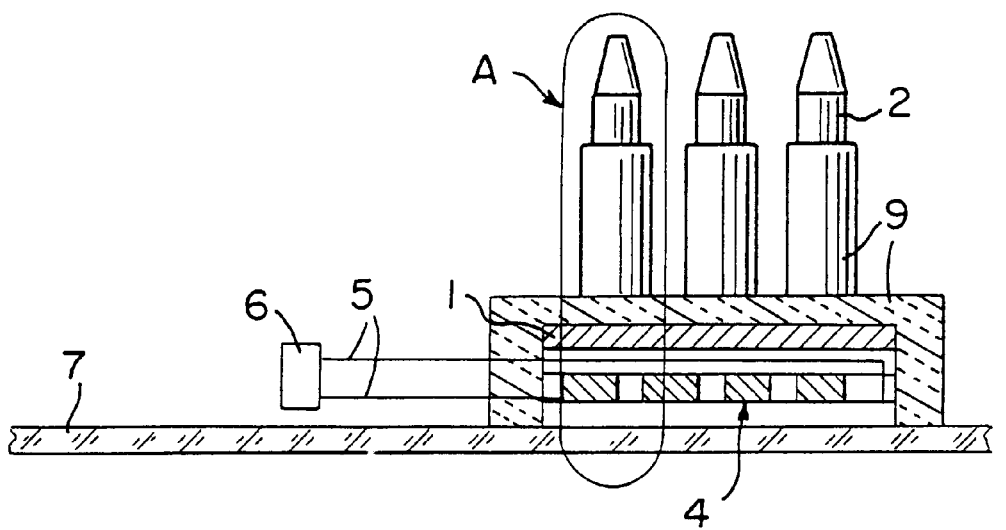
FIG. 2 is a section taken along the line II—II in FIG. 1.
Figure 3:
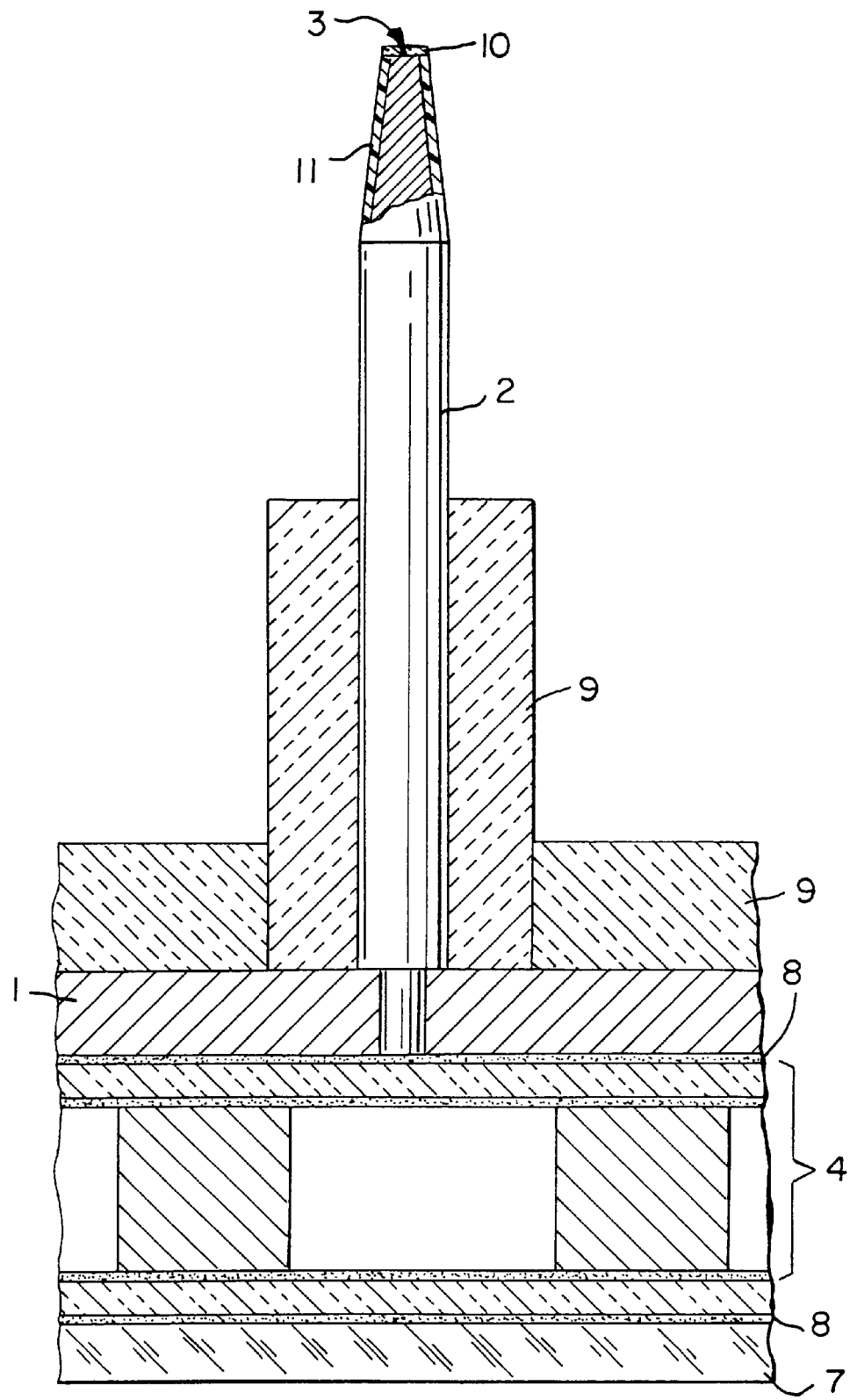
FIG. 3 is a scaled-up view of the portion A in FIG. 2.

The device for microdispensing of aqueous solutions of substances shown in FIGS. 1, 2, 3 comprises base 1 shaped as a rectangular plate, one side of which carrying a plurality of rods 2 is held with one of their ends to said plate, said rods being arranged parallel to one another and spaced equidistantly to one another. Butt ends 3 of the rods 2 are coplanar with one another and parallel to base 1. Battery 4 of thermoelectric cells adjoins base 1 on the side opposite to that equipped with the rods 2 and is in heat contact therewith, said battery 4 being in this particular embodiment that of Peltier cells shaped as a plate equal in size to the base 1. The battery 4 is connected, through wires 5, to a controlled source 6 of direct-current. The battery 6 of Peltier elements is in fact a means for maintaining the temperature of the butt ends 3 of the rods 2 equal essentially to the dew point of the ambient air. With its other side the battery 4 of Peltier elements adjoins the surface of a flow-block radiator 7 and is in heat contact therewith. To provide a uniform heat contact between the surface of the battery 4 of thermoelectric cells and the base 1 on the one side, and between the radiator 7 on the other side, provision is made for thin (under 100 μm-thick) layers 8 of a heat-conductive paste based on beryllium oxide and polydimethylsiloxane oil.

The base 1 and the rods 2 are made from a material having high thermal conductivity, preferably from a metal, such as copper or brass. Used as the radiator 7 can be silicon slab.

The rods 2 are provided with a heat-insulating coating 9 applied to half their length counting from the point of the rod attachment to base plate 1. Used as a material for said coating can be polyolefin (cf. Heat Shrinkable Pack, RS Components Ltd. Catalogue Nov. 1992—February 1993, England, p. 51, stock No. 399899). A similar heat-insulating coating 9 (foamed polyurethane) is used to protect the surfaces of the base 1 that are exposed to atmospheric air.

The rods 2 in this particular embodiment are round in cross-section (though they may have any other cross-sectional shape) and their vacant ends are shaped as cone frustums tapering to the ends. A hydrophilic coating 10, e.g., glass or gold, is applied to the butt ends 3 of the rods 2, whereas a hydrophobic coating 11, e.g., fluoroplastic or glass whose surface is hydrophobized by treatment with Repel Silane, is applied to the side surfaces of the vacant ends of the rods 2.

The area of the butt ends 3 of the rods 2 is selected such as to obtain the required volume V of the dose being transferred and to obey the following relationship: $V \approx \frac{1}{3}\pi R^3 \cdot 10^{-6}$ nl, where V is the required volume of the droplet forming on the butt rod end after the rod has been withdrawn from the solution, R(μm) being the radius of the butt rod end.

The device carrying into effect the method, according to the invention, is used as follows.

Figure 4:
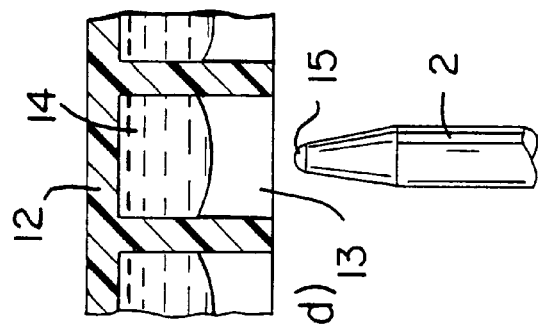
FIGS. 4a, 4b, 4c, 4d are a longitudinal sectional view of a fragment of the tray carrying the solution and the rod at the various stages of the sampling process.
Figure 4:
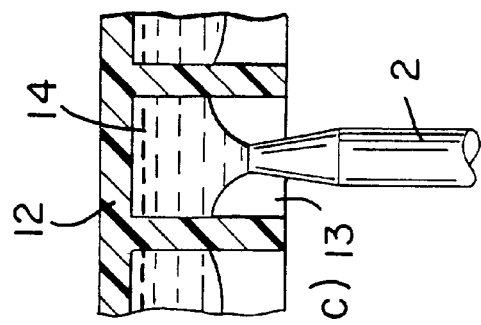
Figure 4:
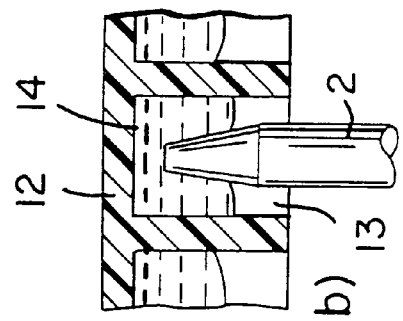
Figure 4:
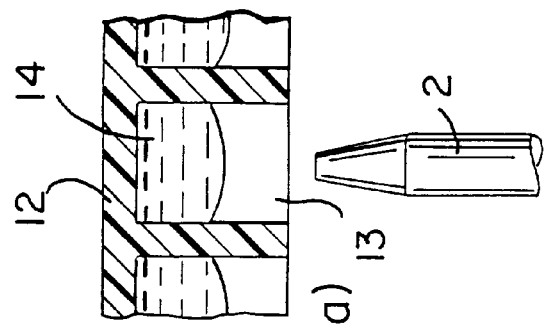
Figure 5:
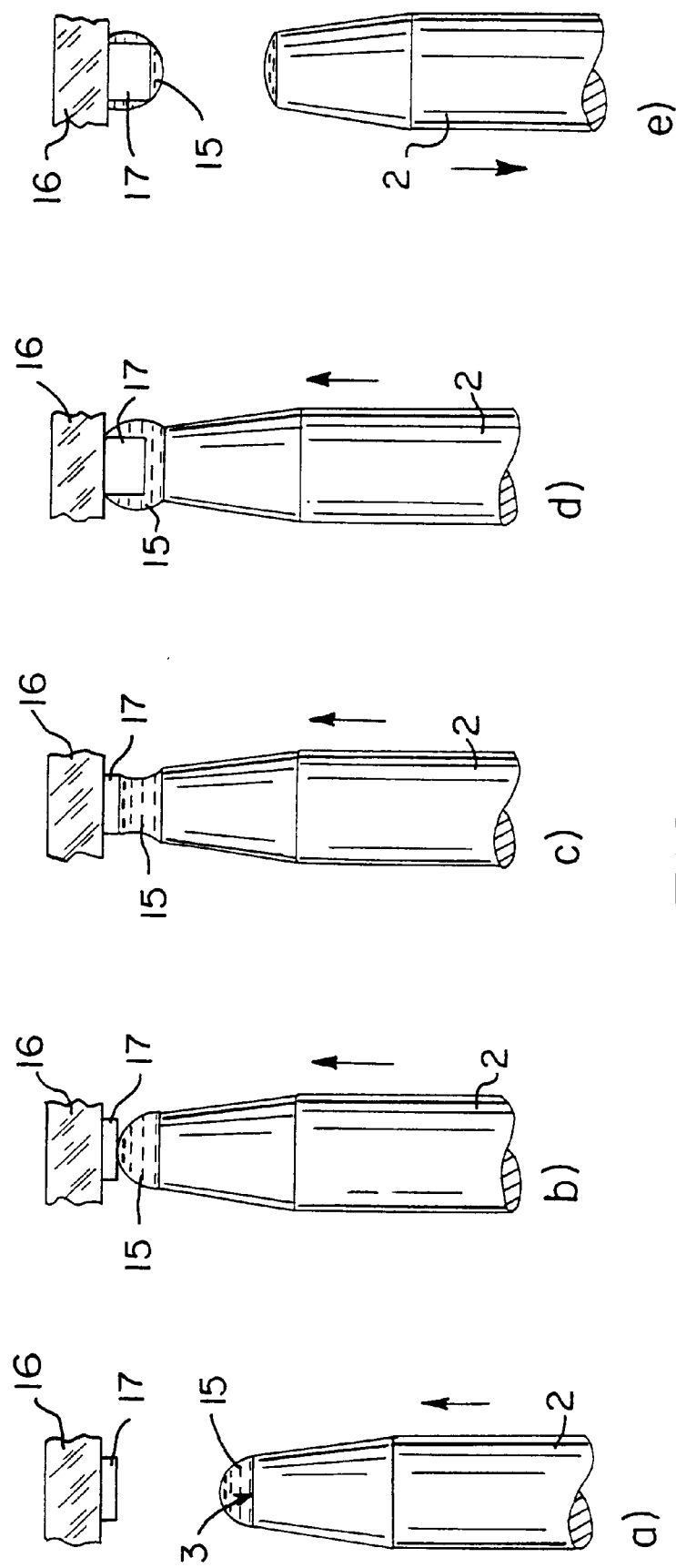
FIGS. 5a, 5b, 5c, 5d are a longitudinal sectional view of a fragment of the carrier and the rod shown at the various stages of sample application.

The base 1 carrying the rods 2 are positioned opposite to the tray 12 (FIG. 4a) in such a manner that each rod 2 is located against a respective well 13 of the tray 12 filled with an aqueous solution 14 of the substance to be transferred, e.g., an aqueous oligonucleotide solution. Then the base 1 is displaced towards the tray 12 until the ends of the rods 2 (FIG. 4b) are dipped into the solution 14. Then, by displacing the base 1 together with the rods 2 (FIG. 4c) in the opposite direction, the rods 2 are withdrawn from the solutions, with the result that a microdose 15 (FIG. 4d) of the solution of the substance is formed on the butt end of each rod 2, the volume V of said microdose being independent of the depth of immersion of the rod 2 into the solution 14 (due to the hydrophilic butt end of the rod and hydrophobic coating on the rod's side surface with respect to the solution being transferred) and being determined substantially by the radius R alone of the butt end of the rod 2. Next the base together with the rods loaded with the microdoses of the solution is transferred to the carrier, e.g., a micromatrix 16 (FIG. 5a) on the glass surface of which are areas 17 of gel, said areas being regularly spaced so as to follow the layout of the rods 2. Then the base is positioned opposite to the surface of the matrix 16 so that each rod 2 is located against the respective gel area 17. Thereupon the base is displaced towards the matrix 16 (FIG. 5b) along the arrow B until the microdoses 15 get in contact with the gel areas 17. The temperature of the solution 14 in the wells 13 of the tray 12 and that of the butt ends 3 of the rods 2 are maintained, during sampling the microdoses from the wells 13 of the tray 12 and transferring them to the matrix 16 to get in contact therewith, substantially equal to the dew point of the ambient air, thus preventing altogether evaporation of the solution during transferring of a microdose. Control of the temperature of the butt ends of the rods 2 and its maintaining at a pressure level are attained by changing the battery 4 voltage of thermoelectric cells (FIGS. 2, 3) in response to the signal produced by a temperature transmitter (not shown) which is in heat contact with the base 1. Gel absorbs vigorously the solution (FIG. 5c), with the result that the gel areas 17 (FIG. 5d) swell and the microdoses 15 (FIG. 5c) are drawn into gel. The base with the rods 2 is retracted from the micromatrix. Once the rods 2 have been washed and dried the device is ready for a next cycle.

The device, according to the invention, makes it possible to effect transference of microdoses of aqueous solutions of substances having a volume of from 0.3 to 50 nl with a high degree of accuracy which, in turn, enables one to simplify the procedure of an oligonucleotide micromatrix preparation, to decrease consumption of expensive materials and to miniaturize the micromatrix.

For better understanding of the present invention, some exemplary embodiments of the invention will be described below that corroborate practicability of the proposed method and device, as well as exactness and reproducibility of microdispensing.

EXAMPLES OF THE INVENTION

Example 1

The task is to microdispense oligonucleotide solutions of a required concentrations, namely solutions of such oligonucleotides as used for immobilization on a solid carrier. To this end, the solutions of oligonucleotides of the following concentrations are prepared: 1.0 nmole/μl; 10 pmole/μl; 100 pmole/μl in a 0.001% bromophenol blue solution in distilled water. The solutions are loaded to the tray wells from one-fourth to two-thirds of their full depth.

The radius R of the butt rod end is 110 μm in this embodiment of the device.

The rod is dipped into the prepared solutions, then is withdrawn therefrom, with the result that a volume of the solution is formed on this butt end of the rod, shaped as a fragment of a hemisphere. It has been found from a run of 10 measurements that the hemisphere-shaped droplets of solutions evaporate for four seconds at an air temperature of 23° C. and a relative humidity of 70±10%.

Then the temperature of the prepared solutions in the tray is adjusted and maintained substantially equal to the dew point for the surrounding conditions at the instant of taking measurements. The same is done with respect to the rod temperature.

The measurement cycle is as follows. The rod is dipped into the solutions for different depths and is then withdrawn therefrom, with the result that a hemisphere-shaped volume of the solution is formed on the butt rod end, whereupon the rod is kept for 2÷15 minutes in the aforementioned state. At the same time, with the aid of MBS-10 microscope provided with an eyepiece having an index dial (X57.5, dial division value 14 μm), the formation and change of microvolumes of the solutions on the butt rod ends, are followed by measuring the height of a part of the hemisphere-shaped volume of the solution. Then the sample is transferred onto a dry nylon filter (Hybond-N+, Amersham International), and the size of the resultant spot is measured. It has been established from a run of 20 measurements that the height of the droplets forming on the butt rod end remains invariable, within the used range of concentrations and, within the limits of the division value of the instrument scale (i.e., is independent of the concentration of the solutions of oligonucleotides within the measurement error), the size of the spots on the filter is the same within the limits of the instrument scale division value, which confirms the exactness and reproducibility of the method. Similar measurements have been taken, yielding the same results, using the film of polyacrylamide gel having a thickness of 5 μm and formed on the glass surface as the carrier.

Example 2

Determining the exactness and reproducibility of the method.

Reproducibility and exactness of the proposed method are determined against the dilution of a dose of the dye solution transferred, with the aid of the proposed device, to a known volume of distilled water and by measuring the degree of dilution against light absorption at a wavelength close to the absorption peak for a given dye. When the radius R of the butt rod end is equal to 100 the estimated volume of a droplet formed on the butt rod end is approximately 1.4 nl. Dilution of said dose in a 500-μl volume of distilled water will be $5 \times 10^5$ times.

There is prepared a solution of the dye Safranin MN in distilled water, saturated at room temperature. The solution is filtered through a glass filter having pores of 100 μm diameter, diluted by 20% and used as a parent solution for all measurements that follow.

The spectrophotometer Shimadzu UV-VIS, Model UV-160 (Shimadzu Corporation) is used for measuring the absorption spectra.

There are prepared samples of said parent solution of said dye by diluting it with distilled water by $10^3$ and $10^5$ times, and the absorption spectrum is measured for the prepared samples in the vicinity of the peak region for Safranin MN. Then the peak signals on the spectra are measured and the ratio therebetween is calculated. The ratio between the signals for said two samples is 98, which lends support to a possibility of using the parent solution for measuring the peak signals of absorption spectra for the samples with the parent solution diluted up to $10^5$ times (the expected dilution ratio is $5 \times 10^5$). Dependence of the measured signal S at the absorption peak can be found from the expression $$S_0 = k'/r \quad (1),$$

where k' is the proportionality factor found from (1) with the parent solution dilution ratio $r=10^3$, r is the dilution ratio determined from the relationship $$r = \frac{V_d + V_k}{V_k}, \quad (2)$$

where $V_d$ is the volume of distilled water, $V_k$ is the sample volume containing the dye. Since $V_k \ll V_d$, then $$r \approx \frac{V_d}{V_k}, \quad (3)$$

proceeding from (2). Having substituted (3) into (1), we obtain $$S = \frac{k'}{V_d} \cdot V_k; \quad (4)$$

denoting $$\frac{V_d}{k'} = k \quad (5)$$

and substituting (5) into (4), we obtain expression $$V_k = S \cdot k \quad (6)$$

for recalculating the measured signals at the peaks of the absorption spectra for a run of measurements, when transferring the parent solution doses from the rod to the volume of distilled water in a measuring cell.

Factor k is calculated from expressions (1) and (5) with the value 'r' equal to $10^3$ for the parent solution, and is 349.50 nl.

Temperature in the present device is adjusted and maintained substantially equal to the dew point under the surrounding conditions, for the whole period of the experiment (the ambient temperature being 20±5° C. and ambient air humidity, 70±10%).

The measuring cycle is as follows. The rod is dipped into the parent solution and then is withdrawn therefrom, with a result that a volume of the parent solution is formed on the butt rod end, shaped as a fragment of a hemisphere and is kept for 2÷10 minutes in said state. Simultaneously observation is made, through the MBS-10 microscope provided with a dial-scale eyepiece (X57.5, dial division value 14 μm), of the formation and change of microvolume of the parent solution on the butt rod end. A clean quartz cell washed with distillate is filled with 700 μl of distilled water and placed in the spectrophotometer, after which the distillate-distillate absorption spectrum is taken, thereby assessing the background F. Next the rod of the device is immersed into said cell so that the parent solution dose is "washed off" from the rod into the cell, and the resultant diluted solution is thoroughly stirred in the cell using a fine glass stick. Then the cell is re-placed in the spectrophotometer and the absorption spectrum of the diluted solution is recorded; the intensity of the signal S at the absorption peak is also measured. All the measurement results are recorded as the spectra by a built-in printer.

Thus, a run of 10 measuring cycles are performed, the measurement results are tabulated in Table 1.

The actual value of the transferred microvolume $\overline{V}$ is found from the following expression:

$$\overline{V} = \frac{1}{n} \sum_{i=1}^{n} V_i, \quad (7)$$

where n is the number of measurement taken;

Vi is the value of the volume of an individual measurement found from Table 1.

The mean-square error of measurement is calculated by the formula:

$$\overline{\sigma} = \sqrt{\frac{1}{n-1} \sum_{i=1}^{n} (V_i - \overline{V})^2} \qquad (8)$$

Since the number of measurements is limited, use is made of the Student distribution law for determining the half-width of the confidence interval $\epsilon_P$:

$$\varepsilon_p = t_p \frac{\overline{\sigma}}{\sqrt{n}}, \qquad (9)$$

where $t_p$ is the Student distribution coefficient for the number 'n' of measurements with a two-sided confidence level 'p' (found from Table 5, in: "Tables of mathematical statistics" by P. Mueller et al., Finansy i Statistika PH, 1982 (in Russian).

TABLE 1

| No. | Background (F) | Signal (S) | Volume, nl (V = (S −F) × K) |
|---|---|---|---|
| 1 | −0.00016 | 0.003889 | 1.414643 |
| 2 | −0.00048 | 0.005079 | 1.941667 |
| 3 | 0 | 0.005159 | 1.802976 |
| 4 | −0.00016 | 0.006508 | 2.33 |
| 5 | −0.00046 | 0.003968 | 1.553333 |
| 6 | −0.00032 | 0.004524 | 1.692024 |
| 7 | 0.000952 | 0.005238 | 1.497857 |
| 8 | 0.000952 | 0.003889 | 1.02631 |
| 9 | −0.00063 | 0.00381 | 1.553333 |
| 10 | 0 | 0.0023571 | 8.238214 |

Then the measurement data tabulated in Table 1 are analyzed, measurement No. 10 is discarded. Errors are calculated using formulas (7), (8), and (9). For n=9 and $t_p$=2.306 the following data are obtained: $\overline{V}$=1.646 nl; $\overline{\sigma}$=0.364 nl; $\epsilon_p$=0.29 nl (with the value of 'p' assumed as 0.95).

That is, with the confidence level of 0.95, the dispensing error equals ±0.29 nl or ±17.6%, whereas the permissible error in dispensing aqueous solutions of oligonucleotides per micromatrix is ±20%. The theoretically estimated value of the volume being transferred (V≈1.4 nl with R=110 µm) is lesser than that established experimentally. This can be explained by the fact that the dye concentration in the parent solution is selected with due account of the lower limit of the spectrophotometer sensitivity. That is why the parent solution has to have a viscosity much higher than the theoretically possible one so that when the rod is withdrawn from the solution the latter covers part of the rod side surface immersed thereinto, with a fine film, which is not the case within the permitted viscosity range for actual solutions of oligonucleotides.

The present method and device are designed for applying microdoses of aqueous solutions, containing biological components, such as DNA fragments, chromosomes, cells, etc. in both fundamental research and for applied tasks, e.g. in medicine and agriculture. Furthermore, the proposed method and device can find use in some other fields of science, technology and national economy whenever it becomes necessary to prepare a great number of equal microvolumes of aqueous solutions of substances, to transfer such microvolumes to the object and introduce them into other solutions or apply to the surface of "solid" bodies, such as gels, glass or porous bodies.

We claim:

1. A device for microdispensing a volume of an aqueous solution to a carrier, comprising:
    (a) a base having a side,
    (b) a plurality of rods, each rod having a base end and a free butt end, wherein the base ends of the rods are held firm against the side of the base and wherein the free butt ends of the rods are coplanar, and
    (c) means for maintaining the temperature of the free butt ends of the rods essentially equal to the dew point of the ambient air.

2. A device for microdispensing a volume of an aqueous solution to a carrier, comprising:
    (a) a base having a side,
    (b) a plurality of rods, each rod having a base end and a free butt end, wherein the base ends of the rods are held firm against the side of the base and wherein the free butt ends of the rods are coplanar, and
    (c) means for maintaining the temperature of the free butt ends of the rods essentially equal to the dew point of the ambient air,
wherein the means for maintaining the temperature of the free butt ends is a thermoelectric battery.

3. The device of claim 2, wherein both the base and the rods are made of a heat-conductive material.

4. The device of claim 3, wherein both the base and the rods are made of metal.

5. The device of claim 2, wherein the battery is in contact with the base.

6. The device of claim 5, wherein the battery is shaped as a plate having the same size as the base and is in contact with the base on a side opposite to the side carrying the rods.

7. The device of claim 6, wherein both the base and the rods are made of a heat-conductive material.

8. A method for microdispensing an aqueous solution to a carrier using a rodlike transferring element, comprising:
    (a) wetting a butt end surface of the transferring element with the aqueous solution of the substance,
    (b) forming on the butt end surface a preset dose of the solution, and
    (c) displacing the transferring element until the dose contacts a surface of the carrier and is transferred,
wherein the temperature of the aqueous solution and the temperature-of the butt end surface of the transferring element are maintained at essentially equal to the dew point of the ambient air during dose formation and transference.

9. A method according to claim 8 wherein the aqueous solution of a substance is an aqueous solution of oligonucleotides.

10. A device for microdispensing a volume of an aqueous solution to a carrier, comprising:
    (a) a rodlike transferring element with a free butt end, and
    (b) means for maintaining the temperature of the free butt end of the transferring element essentially equal to the dew point of the ambient air.

* * * * *